United States Patent
Wagner et al.

(10) Patent No.: US 7,294,505 B2
(45) Date of Patent: Nov. 13, 2007

(54) STABLE EPISOMAL VECTORS

(75) Inventors: Thomas E. Wagner, Greer, SC (US); Xianzhang Yu, Greenville, SC (US)

(73) Assignee: GHC Research Development Corporation, Greenville, SC (US)

( * ) Notice: Subject to any disclaimer, the term of this patent is extended or adjusted under 35 U.S.C. 154(b) by 0 days.

(21) Appl. No.: 10/231,467

(22) Filed: Aug. 30, 2002

(65) Prior Publication Data

US 2003/0064472 A1 Apr. 3, 2003

Related U.S. Application Data

(60) Provisional application No. 60/315,698, filed on Aug. 30, 2001.

(51) Int. Cl.
| | |
|---|---|
| C12N 15/00 | (2006.01) |
| C12P 21/04 | (2006.01) |
| A01N 63/00 | (2006.01) |
| A01N 65/00 | (2006.01) |
| A01N 43/04 | (2006.01) |
| A61K 31/70 | (2006.01) |
| C07H 21/02 | (2006.01) |
| C12N 5/00 | (2006.01) |
| C12N 5/02 | (2006.01) |

(52) U.S. Cl. .................. 435/320.1; 435/70.1; 435/325; 424/93.1; 514/44; 536/23.1

(58) Field of Classification Search ............... 536/23.1, 536/24.1; 514/44; 424/93.1; 435/320.1; 800/21

See application file for complete search history.

(56) References Cited

U.S. PATENT DOCUMENTS

| | | | |
|---|---|---|---|
| 5,591,601 A * | 1/1997 | Wagner et al. | ............. 435/69.1 |
| 6,025,155 A | 2/2000 | Hadlaczky et al. | |
| 6,046,015 A * | 4/2000 | Goodman et al. | ........... 435/7.8 |

OTHER PUBLICATIONS

Langle-Rouault, et al. (1998) J. Virol., 72(7):6181-85.*
Deonarain (1998) Exp. Opin. Ther. Pat., 8(1): 53-69□□.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Wolff, et al. (2001) Nature Biotech., 19: 1118-20.*
Zanta, et al. (1999) Proc. Natl. Acad. Sci., USA., 96: 91-96.*
Aiyar, et al. (1998) J. Biol. Chem., 273(49): 33073-81.*
Yamamoto, et al. (1999) Virus Research, 65: 43-55.*
Miyata, et al. (2000) Oncogene, 19: 1477-84.*
Parnaik, et al. (1990) Molec. Cell. Biol., 10(3): 1287-92.*
Belt et al., "Construction and properties of an Epstein-Barr-virus-derived cDNA expression vector for human cells", *Gene*, 1989, pp. 407-417, vol. 84, Elsevier Science Publishers B. V. (Biochemical Division).
Mazda et al., "Extremely efficient gene transfection into lympho-hematopoietic cell lines by Epstein-Barr virus-based vectors", *Journal of Immunological Methods*, 1997, pp. 143-151, vol. 204, Elsevier Science Publishers B. V.
Durocher et al., "High-level and high-throughput recombinant protein production by transient transfection of suspension-growing human 293-EBNA1 cells", *Nucleic Acids Research*, 2002, pp. e 1-e9, vol. 30, No. 2, Oxford University press.
Rubanyi, "The future of human gene therapy", *Molecular Aspects of Medicine*, 2001, pp. 113-142, vol. 22, Elsevier Science Ltd.
Langle-Rouault et al., "Up to 100-Fold Increase of Apparent Gene Expression in the Presence of Epstein-Barr Virus *on* P Sequences and EBNA1: Implications of the Nuclear Import of Plasmids.", Journal of Virology, The American Society For Microbiology, vol. 72, No. 7, Jul. 1998, pp. 6181-6185, XP002924894 ISSN: 0022-538X.
M. Brisson et al., "A novel T7 RNA polymerase autogene for efficient cytoplasmic expression of target genes.", Gene Therapy, vol. 6, No. 2, Feb. 1999, pp. 263-270, XP002302503, ISSN: 0969-7128.
S. Wang et al., "A novel herpesvirus amplicon system for in vivo gene delivery.", Gene Therapy, vol. 4, No. 11, Nov. 1997, pp. 1132-1141, XP000964755, ISSN: 0969-7128.
Kathleen Van Craenenbroeck et al., "Episomal vectors for gene expression in mammalian cells.", European Journal of Biochemistry, vol. 267, FEBS 2000, pp. 5665-5678, XP002954557, ISSN: 0014-2956.

* cited by examiner

*Primary Examiner*—Joseph Woitach
*Assistant Examiner*—Robert M. Kelly
(74) *Attorney, Agent, or Firm*—Foley & Lardner LLP

(57) ABSTRACT

The present invention provides a vector system which can be stably translocated from the cytoplasm of a cell to the nucleus where it is a stable nuclear episomal vector. A basic vector system according to the present invention is generally composed of nucleic acid encoding (a) a promoter functional both in cytoplasm and nucleus, operably linked to (b) a plasmid maintenance/translocation factor and (c) an origin of replication.

13 Claims, 1 Drawing Sheet

STABLE EPISOMAL VECTORS

BACKGROUND OF THE INVENTION

Current eukaryotic vector technologies can be divided into two basic categories, viral and non-viral vectors. Viral vectors tend to be much more efficient in terms of delivery, maintenance and overall expression levels. They suffer, however, from the need to be infective, which raises obvious safety concerns and implicates complicated processing technologies, like packaging systems and helper viruses.

Non-viral systems are considered more desirable because of their more defined characteristics, but the suffer from delivery and stability problems. One such problem is that typical delivery systems do not efficiently provide the vector in the nuclear context, where it is best maintained and expressed.

It is desirable, therefore, to develop a vector system that efficiently mediates transfer from the cytoplasm to the nucleus, where more efficient gene expression is possible. Moreover, it is desirable to provide a stable episomal vector that has a higher copy number than the chromosome.

SUMMARY OF THE INVENTION

In view of the foregoing deficiencies in the art, it is an object of the invention to provide a basic vector system comprising nucleic acid encoding (a) a promoter functional both in cytoplasm and nucleus operably linked to a plasmid maintenance/translocation factor and (b) an origin of replication. In some embodiments, the plasmid maintenance/translocation factor is EBNA-1. In other embodiments, the origin of replication is oriP. In different embodiments, the promoter functional in both cytoplasm and nucleus comprises one or more nuclear and/or cytoplasmic promoters. In a preferred embodiment, the plasmid maintenance/translocation factor is EBNA-1, the promoter functional both in cytoplasm and nucleus comprises T7 promoter and SV 40 promoter and the origin of replication is oriP.

In some embodiments, the vector system comprises nucleic acid encoding the components of the basic vector system and further comprises nucleic acid encoding additional components. For example, in addition to the components of the basic vector system in one embodiment the vector system comprises nucleic acid encoding a poly cloning site operably linked to a nuclear promoter. The polycloning site may contain a nucleotide sequence encoding, for example, a gene of interest. In another embodiment, the basic vector system further comprises nucleic acid encoding one or more selection markers functional in prokaryotes and/or eukaryotes. In another embodiment, the basic vector system further comprises nucleic acid encoding a bacterial origin of replication. In addition, the present invention provides a method of gene therapy involving administering the vector system described above to a patient.

DETAILED DESCRIPTION OF THE INVENTION

Figure 1:
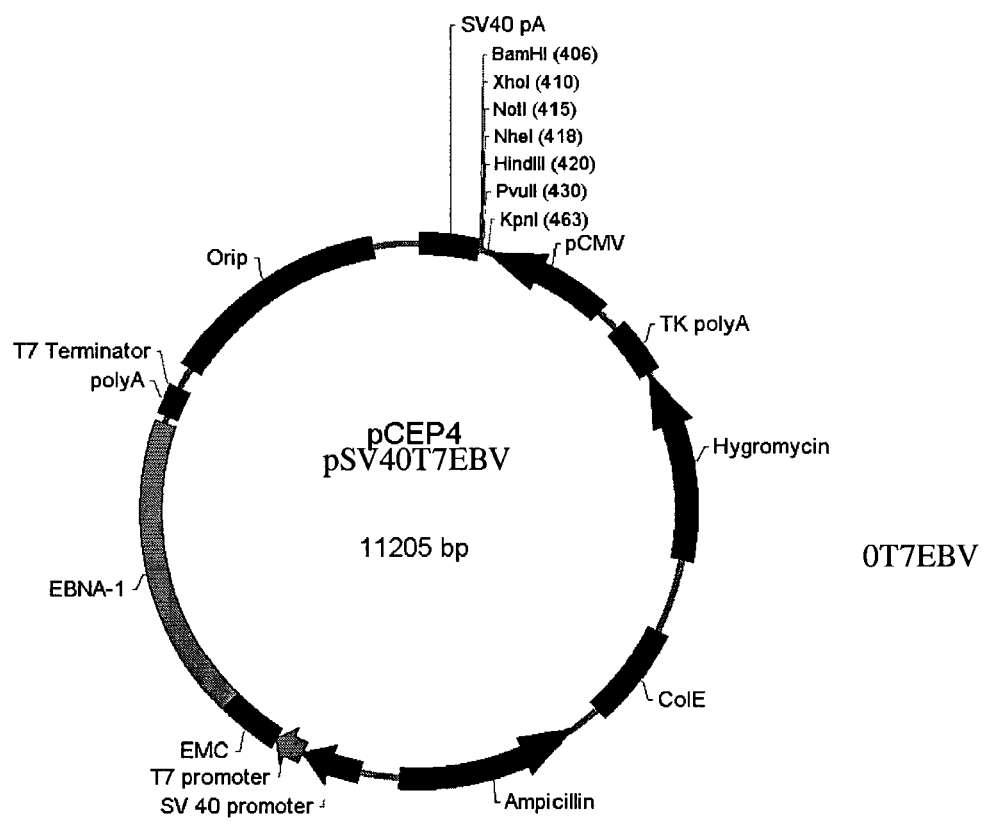
FIG. 1 illustrates a vector system of the present invention, pSV40T7EBV.

The present invention overcomes two significant problems in the art. First, it expands the normal host range of EBV vectors. Conventional EBV vectors can only be maintained in the nucleus of human cells, not other mammalian cells. This host preference has heretofore greatly limited the applications of EBV vector, since it could not be used in a murine model, for example. This advantage is realized by replacing the endogenous EBV promoter with a promoter that functions in a wider range of cells, like an SV40 promoter.

Second, it increases the transfection efficiency of conventional EBV vectors. Vectors that function in the nucleus, like EBV vectors, must pass through two barriers during the transfection process, i.e., the cytoplasmic membrane and the nuclear membrane. Most of the prior research focused on trying to optimize the transfection efficiency are, thus, focused on the first barrier. In the present invention, the transfection efficiency is increased by overcoming the second barrier, i.e., the nuclear membrane barrier. To accomplish this, the invention incorporates a promoter that functions in the cytoplasm, like a cryptic cytoplasmic T7 promoter, between the nuclear promoter and the translocation/maintenance factor gene sequence, like EBNA-1. The translocation/maintenance factor gene sequence functions not only to support the episomal replication of the vector but also facilitates translocation of the vector from cytoplasm to the nucleus. The present invention provides a vector system which, upon conventional delivery to the cytoplasm, can be more efficiently translocated from the cytoplasm of a cell to the nucleus where it is stably propagated as a nuclear episomal vector.

A basic vector system according to the present invention is composed of nucleic acid encoding (a) a first promoter region functional both in cytoplasm and nucleus, operably linked to (b) a plasmid maintenance/translocation factor and (c) an eukaryotic origin of replication. Preferred vectors also contain a second, nuclear promoter, operably linked to a cloning site for convenient insertion of a target gene—a gene it is desired to express.

As used herein, a "translocation" factor is a gene product that is capable of mediating the transfer of a nucleic acid from the cytoplasm to the nucleus. A preferred plasmid translocation factor is EBNA-1, derived from Epstein Barr virus. Other such translocation factors are contemplated to be equally functional in the present vector system.

A "maintenance" factor is a gene product, which promotes replication and/or segregation of an episomal vector. In that way, it promotes coordinate replication of the episomal vector and/or its segregation during cell division, thereby increasing the probability that it is maintained in the progeny. EBNA-1is such a factor, as it is required for replication from the EBV origin of replication. T-antigen of SV-40 is another example.

As used herein, the term "operably linked" is used to mean when two sequences of a nucleic acid molecule are linked to each other in a manner which either permits both sequences to be transcribed onto the same RNA transcript, or permits an RNA transcript, begun in one sequence, to be extended into the second sequence. Thus, two sequences, such as a promoter sequence and any other "second" sequence of DNA are operably linked if transcription commencing in the promoter sequence will produce an RNA transcript of the operably linked second sequence. In order to be "operably linked" it is not necessary that two sequences be immediately adjacent to one another.

The promoter functional in both cytoplasm and nucleus is any promoter functional in both cytoplasm and nucleus. Typically, it is a hybrid promoter and, in such cases, may more properly be termed a promoter "region." Hence, the promoter may be a single promoter or a hybrid comprising one or more cytoplasmic and/or nuclear promoters. Since eukaryotic promoters typically are only functional in the nucleus—that is the situs of the RNA polymerase—for a promoter to be functional in the cytoplasm, the nucleic acid generally is delivered with the cognate RNA polymerase bound to the promoter. As described below, this allows a small amount of the encoded translocation factor to be produced, which mediates translocation of the plasmid to the nucleus, where host RNA polymerases can mediate further transcription.

The promoter sequences of the present invention may be either prokaryotic, eukaryotic or viral. Suitable promoters are repressible and/or inducible. Examples of suitable prokaryotic promoters include those derived from phage, like T4 (Malik, S. et al., J. Biol. Chem. 263:1174-1181 (1984); Rosenberg, A. H. et al., Gene 59:191-200 (1987); Shinedling, S. et al., J. Molec. Biol. 195:471-480 (1987); Hu, M. et al., Gene 42:21-30 (1986)), T3, Sp6, and T7 (Chamberlin, M. et al., Nature 228:227-231 (1970); Bailey, J. N. et al., Proc. Natl. Acad. Sci. (U.S.A.) 80:2814-2818 (1983); Davanloo, P. et al., Proc. Natl. Acad. Sci. (U.S.A.) 81:2035-2039 (1984)), and the $P_R$, int and $P_L$ promoters of bacteriophage λ (The Bacteriophage Lambda, Hershey, A. D., Ed., Cold Spring Harbor Press, Cold Spring Harbor, N.Y. (1973); Lambda II, Hendrix, R. W., Ed., Cold Spring Harbor Press, Cold Spring Harbor, N.Y. (1980)).

Bacterial promoters include the trp, recA, heat shock, and lacZ promoters of *E. coli*; the α-amylase (Ulmanen, I., et al., J. Bacteriol. 162:176-182 (1985)) and the σ-28-specific promoters of *B. subtilis* (Gilman, M. Z., et al., Gene 32:11-20 (1984)); *Bacillus* and *Streptomyces* promoters (Ward, J. M., et al., Mol. Gen. Genet. 203:468-478 (1986)); the; the bla promoter of the .beta.-lactamase gene of pBR322, and the CAT promoter of the chloramphenicol acetyl transferase gene of pPR325, etc. Prokaryotic promoters are reviewed by Glick, B. R. (J. Ind. Microbiol. 1:277-282 (1987)); Cenatiempo, Y. (Biochimie 68:505-516 (1986)); Watson, J. D. et al. (In: Molecular Biology of the Gene, Fourth Edition, Benjamin Cummins, Menlo Park, Calif. (1987)); and Gottesman, S. (Ann. Rev. Genet. 18:415-442 (1984)).

Exemplary eukaryotic promoters include the promoter of the mouse metallothionein I gene (Hamer, D., et al., J. Mol. Appl. Gen. 1:273-288 (1982)); the TK promoter of Herpes virus (McKnight, S., Cell 31:355-365 (1982)); the SV40 early promoter (Benoist, C., et al., Nature (London) 290: 304-310 (1981)); and the yeast gal4 gene promoter (Johnston, S. A., et al., Proc. Natl. Acad. Sci. (USA) 79:6971-6975 (1982); Silver, P. A., et al., Proc. Natl. Acad. Sci. (USA) 81:5951-5955 (1984)).

Preferred eukaryotic origins of replication are of viral origin, like OriP of EBV. They may be derived, for example, from Herpesviruses, EBV, papillomaviruses, SV-40 and the like. As for yeast, the 2 micron circle origin also can be used.

In addition to comprising nucleic acid encoding the components of the basic vector system described above, the vector system may further comprise nucleic acid encoding additional components. For example, the vector system may also contain nucleic acid encoding a multiple cloning site, operably linked to a promoter that functions in the nucleus. The multiple cloning site contains more than one restriction endonuclease cleavage site which facilitates cloning (and thus expression) of a target gene. Exemplary restriction endonucleases are BamHI, XhoI, NotI, NheI, HindIII, PvuII and KpnI.

The promoter driving expression of the target gene may be any promoter operable in the nucleus. Exemplary nuclear promoters are metallothionine, alpha-actin, CMV immediate early, HSV thymidine kinase, early and late SV40, and LTRs from retroviruses. A preferred nuclear promoter is CMV immediate early.

A target genes is any gene for which it is desirable to express the gene product. This can be either for the purpose of isolating the gene product, which generally is a protein, but may be an RNA, or for a direct therapeutic purpose. The target gene also can be a marker, such as green fluorescent protein or beta-galactosidase.

In a preferred embodiment of the invention, the vector further comprises a nucleic acid encoding one or more selectable markers, which are functional in prokaryotes and/or eukaryotes. Exemplary selection markers confer resistance to ampicillin, tetracyline, rifampicin, streptomycin, kanamycin and hygromycin. Other markers may be metabolically based and confer, for example, the ability to synthesize specific amino acids or otherwise complement a host metabolic deficiency.

Typically, and inventive vector further comprises a bacterial origin of replication, which facilitates large scale production of the vector in a bacterial system. Exemplary bacterial origins of replications are derived from bacteria, their plasmids or viruses. Preferred bacterial origins of replication include ColE1, ColE1 derivatives (like the pUC origin), any of the R6K origins, oriC, the origin from pSC101.

The inventive vector also generally contains standard features that aid in protein production, such as poly-adenylation sites. Exemplary poly A sites include those derived from HSV TK and SV40. A particularly preferred vector has the features of pSV40T7EBV (see FIG. 1).

Utility/Methods/Science

The vectors of the invention are useful either in the laboratory or clinical settings. Because they do not integrate with any regularity into the chomosome, there is little danger of insertional mutagenesis, or other problems associated with conventional vector systems. Moreover, since the vectors of the invention contain a maintenance factor, they are stably replicated along with the cellular chromosomal complement and are not lost with cell division. Hence, they can be used, for example, as expression vectors, for production of industrially important gene products or they may be used for gene therapy technology in methods of treatment.

A typical method of producing a target protein would entail culturing a host cell that bears an inventive vector under conditions whereby the target protein is expressed. Where the target protein is controlled by an inducible promoter, appropriate conditions (e.g, temperature for thermally inducible promoters) for induction are provided. The inventive plasmid is introduced into a host cell using conventional methods and the resultant protein or RNA may be isolated using conventional purification techniques.

A typical therapeutic method involves contacting a target cell—one in which target gene expression is desired for therapeutic purposes—with a vector encoding a target gene, such that the vector is taken into the target cell. The target cell may be contacted via systemic or direct administration, depending on the disorder to be treated and the nature of any accessory components, like specific cell targeting components. The target cell also may be contacted ex vivo and then introduced into a patient. The vector should be administered in a therapeutically effective amount, which is an amount needed to affect at least one symptom or therapeutic marker of the disorder being treated.

As noted, the methods of the invention rely on conventional delivery to a target cell. The vectors can be delivered in vitro or in vivo. Conventional techniques include calcium phosphate precipitation, electroporation and liposome-mediated delivery, among others. In fact, where desirable, viral components may be included in the vector so that it may be packaged and thereby delivered to the target cell via normal viral delivery pathways.

Prior to delivering the vector to a target cell, however, the promoter that functions in the cytoplasm is pre-bound with an RNA polymerase. In the case of phage promoters, for example, the cognate phage polymerase is bound. For a T7 promoter, the T7 RNA polymerase is generally used. A preferable cytoplasmic promoter element is a bacterial or phage promoter, as such promoters require only their cognate RNA polymerase (and mononucleotide building blocks). A particularly preferred promoter element is derived from phage T7, such as the gene 10 promoter, which is employed commercially in bacterial expression systems.

Once the vector is delivered to the cytoplasm, the cytoplasmic promoter is activated, by the pre-bound RNA polymerase, thereby expressing the encoded translocation factor. The translocation factor encodes a gene product that mediates transfer of the vector to the nucleus of the target cell. The translocation factor may also be a maintenance factor, as set out above.

After the vector is translocated into the nucleus, the nuclear promoter element drives expression of the maintenance factor, which also may be a translocation factor. The maintenance factor then aids in propagating and generally stabilizing the vector.

What is claimed is:

1. A vector system capable of facilitated translocation from the cytoplasm to the nucleus of a eukaryotic cell, comprising a nucleic acid comprising:
   (a) a promoter element functional both in the cytoplasm and nucleus of a cell which promoter element comprises a T7 promoter or a SP6 promoter, said promoter element being operably linked to:
   (b) a gene sequence for a plasmid maintenance factor and a translocation factor, encoding either (i) EBNA-1 or (ii) EBNA-1 and T-antigen of SV40, and
   (c) a eukaryotic origin of replication, wherein the promoter element is bound to its cognate T7 or SP6 RNA polymerase.

2. The vector system of claim 1 wherein said eukaryotic origin of replication is oriP.

3. The vector system of claim 1 wherein said promoter element is a hybrid promoter.

4. The vector system of claim 1 wherein said promoter element further comprises at least a portion of an SV 40 promoter.

5. The vector system of claim 1, wherein the nucleic acid further comprises a multiple cloning site operably linked to a nuclear promoter.

6. The vector system of claim 5 wherein said multiple cloning site further comprises a nucleic acid sequence encoding a target gene.

7. The vector system of claim 1 wherein:
   (a) said plasmid maintenance factor and said translocation factor are EBNA-1,
   (b) said promoter element comprises a T7 promoter and a SV40 promoter, and
   (c) said eukaryotic origin of replication is oriP.

8. A method of expressing a target gene, comprising culturing a host cell containing the vector system of claim 1, said nucleic acid further comprising a target gene, under conditions that promote expression of said target gene in said host cell.

9. A composition comprising the vector system of claim 1, further comprising a pharmaceutically acceptable carrier, and wherein the nucleic acid further comprises a target gene.

10. A method for facilitating translocation of a vector from the cytoplasm of a target cell to the nucleus of the target cell in vitro comprising:
    (a) incorporating into a vector:
       (i) a promoter element functional in both the cytoplasm and the nucleus of a cell, which promoter element comprises a T7 or SP6 promoter, said promoter element being operably linked to:
       (ii) a gene sequence for a plasmid maintenance factor and a translocation factor, comprising either (i) EBNA-1 or (ii) EBNA-1 and T antigen of SV40, and
       (iii) an eukaryotic origin of replication; and
    (b) contacting the target cell with the vector
    wherein the vector is delivered to the cytoplasm of the target cell and the target cell expresses the translocation and maintenance factor thereby mediating transfer of the vector to the nucleus of the target cell, and
    wherein (i) the translocation factor facilitates translocation of the vector into the nucleus of the cell, and (ii) the promoter is bound to its cognate T7 or SP6 RNA polymerase prior to said step of contacting.

11. The method of claim 10, wherein the vector is an EBV vector that comprises a T7 promoter and a SV40 promoter, and the maintenance and translocation factors are EBNA-1.

12. The vector system of claim 1 wherein the nucleic acid further comprises a prokaryotic origin of replication.

13. The method of claim 10, wherein the nucleic acid further comprises a prokaryotic origin of replication.

* * * * *